United States Patent [19]
Helmchen et al.

[11] Patent Number: 5,693,820
[45] Date of Patent: Dec. 2, 1997

[54] RUTHENIUM COMPLEXES WITH A CHIRAL, BIDENTATE PHOSPHINE/OXAZOLINE LIGAND FOR ENANTIOSELECTIVE TRANSFER HYDROGENATION OF PROCHIRAL KETONES

[75] Inventors: Günther Helmchen, Heidelberg; Thomas Langer, Dossenheim, both of Germany

[73] Assignee: BASF Aktiengesellschaft, Ludwigshafen, Germany

[21] Appl. No.: 777,743

[22] Filed: Dec. 20, 1996

[30] Foreign Application Priority Data

Dec. 22, 1995 [DE] Germany ............ 195 48 399.5

[51] Int. Cl.[6] .................................. C07D 263/10
[52] U.S. Cl. ................ 548/101; 548/104; 548/106
[58] Field of Search .......................... 548/101, 104, 548/106

[56] References Cited

PUBLICATIONS

J. American Chemical Society, vol. 117, p. 7562, Noyori et al, 1995.

*Primary Examiner*—Joseph McKane
*Attorney, Agent, or Firm*—Keil & Weinkauf

[57] ABSTRACT

Ruthenium complexes with a chiral ligand of the general formula:

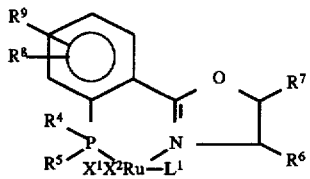

are used for the enantioselective transfer hydrogenation of prochiral ketones.

9 Claims, No Drawings

RUTHENIUM COMPLEXES WITH A CHIRAL, BIDENTATE PHOSPHINE/ OXAZOLINE LIGAND FOR ENANTIOSELECTIVE TRANSFER HYDROGENATION OF PROCHIRAL KETONES

The present invention relates to chiral ruthenium complexes of the general formula (I)

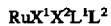   (I)

with a chiral ligand $L^2$, which are suitable for the enantioselective transfer hydrogenation of prochiral ketones.

The enantioselective hydrogenation of prochiral ketones in the presence of chiral rhodium or ruthenium complexes is very important in the preparation of optically active compounds. The complexes which are used contain in most cases a chiral diphosphine ligand whose preparation is complicated and usually includes a technically elaborate and costly racemate resolution. These disadvantages have to date made industrial utilization of these complexes difficult and uneconomic. The use of hydrogen as reducing agent in turn as a rule requires high-pressure apparatus, which results in high operating costs.

Currently used beside catalytic hydrogenation with hydrogen are enantioselective transfer hydrogenations in the presence of chiral rhodium and ruthenium complexes. However, the catalytically active complexes as a rule likewise contain diphosphine ligands which are complicated to prepare. In addition, only moderate enantiomeric excess can be obtained on use of these complexes. Thus, Genêt et al. (Synlett 1993, 478) describe a ruthenium complex with chiral diphosphine ligands which, in the best case, affords an enantiomeric excess of 62% (ee) in the transfer hydrogenation of acetophenone.

Noyori et al. (J. Am. Chem. Soc. 1995, 117, 7562) describe a ruthenium complex which has chiral N-(p-tosyl)-1(S),2(S)-diphenylethylenediamine as ligand and which affords as catalyst high enantiomeric excesses in transfer hydrogenation of prochiral ketones. However, the space-time yield is rather moderate and the system reacts sensitively to steric hindrance in the substrate. Thus, reduction of acetophenone is smooth but that of isobutyrophenone is nonexistent.

Mathieu et al. (J. Chem. Soc. Chem. Comm. 1995, 1721) describe a ruthenium complex with a bidentate, chiral ligand, which has P, N, O as donor atoms. This complex is a very efficient catalyst for transfer hydrogenation of ketones. However, no enantioselectivity is observed on use of prochiral ketones.

It is an object of the present invention to provide a better catalyst for transfer hydrogenation of prochiral ketones. It is particularly intended that the catalyst be easily obtainable, ensure high enantioselectivity and be useable for reducing ketones of any type.

We have found that this object is achieved by complexes of the general formula (I),

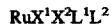   (I)

where $X^1$ and $X^2$ are identical or different and are a halide ion, the anion of a $C_1$–$C_{10}$-carboxylic acid which may have 1, 2 or 3 chlorine or fluorine atoms, the anion of methanesulfinic acid or of trifluoromethanesulfinic acid, or $X^1$ and $X^2$ together are the dianion of a 1,3-, 1,4- or 1,5-dicarboxylic acid, $L^1$ is a cyclic ether with 5–6 ring atoms,
a cyclic olefin with 5–8 ring atoms,
an aromatic compound which may have 1, 2 or 3 alkyl groups as substituents,
CO, PF$_3$, isobutene or
a ligand of the general formula (II)

$$PR^1R^2R^3 \qquad (II)$$

where $R^1$, $R^2$ and $R^3$ are identical or different and are an alkyl group, cycloalkyl group or aryl group, which may have 1, 2 or 3 substituents which are selected, independently of one another, from $C_1$–$C_4$-alkyl groups or $C_1$–$C_4$-alkoxy groups, $L^2$ is a bidentate, chiral ligand of the general formula (III)

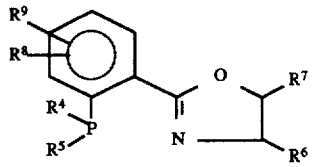   (III)

where $R^4$ and $R^5$ are identical or different and are an alkyl group, cycloalkyl group or aryl group, which may have 1, 2 or 3 substituents which are selected, independently of one another, from alkyl groups, alkoxy groups or halogen atoms, it also being possible for one of the $R^4$ or $R^5$ radicals to be a hydrogen atom, or where $R^4$ and $R^5$ are, together with the phosphorus atom to which they are bonded, a saturated $C_5$–$C_7$-ring, which may be fused to one or two aryl nuclei, $R^6$ is an alkyl group which may have one or more groups which are selected from OH, NH$_2$, SH, COOH, aryloxy, alkoxy, arylthio, alkylthio, acyloxy, alkoxycarbonyl, acylamino, or an aralkyl group, hetaralkyl group, aryl group or hetaryl group, $R^7$ is hydrogen, an alkyl, aryl or aralkyl group, $R^8$ and $R^9$ are identical or different and are hydrogen, $C_1$–$C_4$-alkyl or $C_1$–$C_4$-alkoxy groups, or $R^8$ and $R^9$ together are a fused cycloalkyl or aryl ring, where the absolute configuration at the carbon atoms which carry $R^6$ and $R^7$ is (S) or (R) independently of one another.

In the present application, alkyl is a straight-chain or branched alkyl group with preferably 1 to 6 and, in particular, 1 to 4 carbon atoms. Examples of alkyl groups are methyl, ethyl, n-propyl, i-propyl, n-butyl, i-butyl, sec-butyl and t-butyl. Corresponding statements apply to alkyl groups in alkoxy, alkylthio, alkoxycarbonyl etc. Cycloalkyl is preferably $C_5$–$C_8$-cycloalkyl and, in particular, cyclopentyl and cyclohexyl. Aromatic compound and aryl are benzene, naphthalene and phenyl, α- or β-naphthyl, respectively. Examples of $C_1$–$C_4$-alkyl substituted aromatic compounds are toluene, mesitylene or p-cymene. The hetaryl groups are preferably 5- or 6-membered and have one or two nitrogen atoms and may contain further aromatic systems fused-on. Examples are pyrrolyl, imidazolyl, pyridyl, pyrimidyl, indolyl, quinolinyl etc. An aralkyl or hetaralkyl group is a monovalent radical in which a $C_1$–$C_4$-alkylene chain carries an aryl or hetaryl group. Acyl is RCO, where R is, in particular, H or $C_1$–$C_4$-alkyl.

The $C_1$–$C_{10}$-carboxylic acids whose anions can be used as ligand $X^1$ or $X^2$ in the complex according to the invention are linear or branched alkanecarboxylic acids which may have 1, 2 or 3 chlorine or fluorine atoms, or are corresponding derivatives of benzoic acid or naphthoic acid. Preferred complexes are those in which, independently of one another, $X^1$ or $X^2$ is halide, in particular chloride, bromide and/or iodide or the anion of a $C_1$–$C_4$-carboxylic acid, in particular acetate, propionate and/or butyrate. Likewise preferred are the anions trichloroacetate, trifluoroacetate, methanesulfinate and trifluoromethanesulfinate. $X^1$ and $X^2$ may furthermore together be the dianion of a 1,3-, 1,4- or 1,5-dicarboxylic acid. By this is meant derivatives of malonic acid, succinic acid or glutaric acid.

Preferred ligands $L^1$ in the complexes according to the invention with the formula (I) are CO, $PF_3$ and 1,5-cyclooctadiene, and phosphine ligands of the general formula (II) in which the groups $R^1$, $R^2$ and $R^3$ are, independently of one another, preferably linear or branched $C_1$–$C_4$-alkyl groups or phenyl groups, which are unsubstituted or substituted by 1, 2 or 3 $C_1$–$C_4$-alkyl groups. They are in particular methyl, ethyl, n-propyl, i-propyl, n-butyl and i-butyl or phenyl, ortho- or para-tolyl, para-isopropylphenyl or mesityl. Very particularly preferred complexes contain as ligand $L^1$ triphenylphosphine, tri-$C_1$–$C_4$-alkylphosphine, tritolylphosphine or trimesitylphosphine.

The groups $R^4$ and $R^5$ in the ligand $L^2$ with the general formula (II) are, independently of one another, preferably $C_1$–$C_4$-alkyl, in particular branched $C_1$–$C_4$-alkyl, or aryl which is unsubstituted or substituted by 1, 2 or 3 $C_1$–$C_4$-alkyl groups. $R^4$ and $R^5$ are particularly preferably, independently of one another, methyl, ethyl, n-propyl, i-propyl, n-butyl, i-butyl, phenyl, ortho- or para-tolyl, mesityl, α- or β-naphthyl. If $R^4$ and $R^5$ form, together with the P-atom to which they are bonded, a hetcyclic ring, then $R^4$ and $R^5$ are preferably together n-butylene, n-pentylene or 2,2'-biphenylene.

$R^6$ in the ligand $L^2$ with the general formula (III) is preferably $C_1$–$C_4$-alkyl, phenyl, $(CH_2)_nX$, where X is phenyl, 4-imidazolyl, 3-indolyl, α- or β-naphthyl, $NH_2$, OH, SH, $SCH_3$, COOH or COO-$C_1$–$C_4$-alkyl, and n is 1, 2 or 3.

$R^6$ is, in particular, methyl, ethyl, propyl, i-propyl, n-butyl, 2-butyl, i-butyl, t-butyl, phenyl and benzyl and, particularly preferably, i-propyl and t-butyl.

Atoms or groups preferred according to the invention for $R^7$ are hydrogen, methyl or phenyl and, particularly preferably, hydrogen.

The absolute configuration of the carbon atoms in the oxazoline moiety which carry the substitutents $R^6$ and $R^7$ can be (R) or (S), independently of one another. Suitable ligands $L^2$ according to the invention are only those in which the configuration at the carbon atom which carries $R^6$ is uniformly (R) or (S).

The ligand $L^2$ is particularly preferably a compound of the formulae (IIIa), (IIIb) or (IIIc) with the (R) or (S) configuration at the carbon atom which carries the alkyl group.

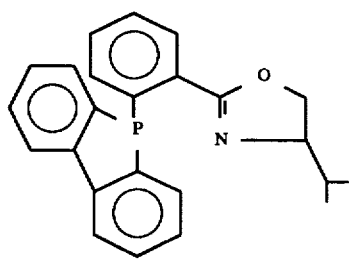

(IIIa)

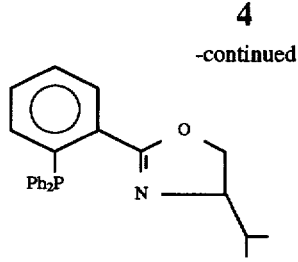

(IIIb)

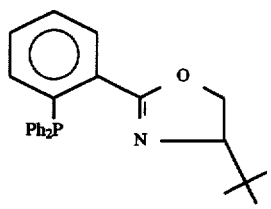

(IIIc)

The preparation of the ligands $L^2$ according to the invention is known or can take place similarly to known methods. They are prepared, for example, starting from chiral amino alcohols of the general formula (V) by an acid-catalyzed ring closure reaction with o-fluoraryl cyanides of the general formula (VI) to give the chiral 2-(o-Fluoraryl)oxazoline derivatives of the general formula (VII) (Bolm et al. Chem. Ber. 1991, 124, 1173). The latter can then be reacted with a suitably substituted phosphine anion to give the required ligand $L^2$ of the general formula (III) (Williamson et al, Synlett, 1993, 509). The groups $R^4$, $R^5$, $R^6$, $R^7$, $R^8$ and $R^9$ in the compounds (III), (V), (VI) and (VII) have the above-mentioned meanings. The chiral amino alcohols can be obtained, for example, starting from chiral amino acids in accordance with the literature quoted in the abovementioned publication(Chem. Ber. 1991, 124, 1173).

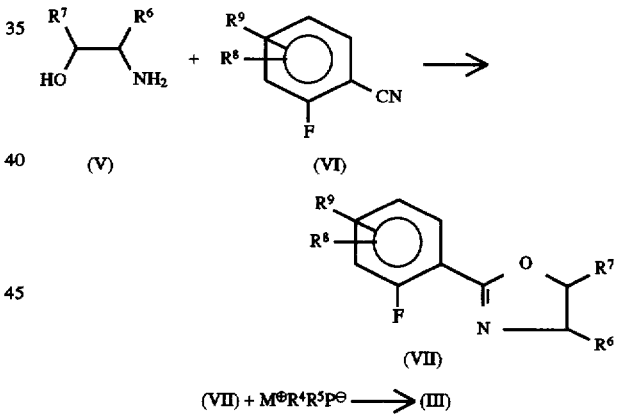

The complexes according to the invention are prepared by reacting a chiral ligand of the general formula (III) with a precursor complex of the formula $RuX^1X^2L^1L^2L^3$, where $X^1$, $X^2$ and $L^1$ have the meanings indicated above, $L^2$ and $L^3$ are identical or different and are selected from CO, aromatic compounds which may have 1, 2 or 3 alkyl substituents, in particular p-cymene, dienes, in particular 1,5-cyclooctadiene (COD), or triarylphosphines, in particular triphenylphosphine. The ligands $L^2$ and $L^3$ may be absent, especially when the precursor complexes are in dimeric or oligomeric form. Examples of suitable complexes are $RuCl_2(PPh_3)_3$, $[RuCl_2(p\text{-cymene})]_2$, $[RuCl_2(COD)]_x$, $[RuCl_2(CO)_3]_2$. The reaction takes place in an inert solvent, for example an aromatic compound which may have 1, 2 or 3 $C_1$–$C_4$-alkyl substituents or chlorine atoms, preferably benzene, toluene, ethylbenzene, p-cymene, chlorobenzene, dichlorobenzene, or an ether, preferably diethyl ether, tetrahydrofuran, methyl t-butyl ether, anisole, or a haloalkane, for example dichloromethane, chloroform, dichloroethane, trichloroethane, at temperatures in the range from 0° C. to 150° C., preferably from 10° C. to 100° C., particularly preferably at room temperature.

Said complexes are suitable as catalysts for the transfer hydrogenation of ketones of the general formula (VIII)

(VIII)

If R and R' are different, the ketones are prochiral, and the transfer hydrogenation for the corresponding alcohols which is catalyzed by the complexes according to the invention is enantioselective. The enantiomeric excess is more than 60% (ee), preferably more than 90% (ee).

There are in principle no restrictions on the nature of the radicals R and R'. They are, independently of one another, straight-chain or branched alkyl, aryl, (het)aryl or (het) aralkyl groups, it being possible for all the groups in turn to have other groups such as alkyl, (het)aryl or (het)aralkyl groups. One of the radicals R and R' is preferably an aryl or hetaryl group. It is also possible for the carbonyl group which is to be reduced to be incorporated in a mono- or polycyclic ring system. Furthermore, the radicals R and R' can have, independently of one another, functional groups. The only restriction on these is that they do not react with the catalyst to decompose it, or that they do not react with the carbonyl group which is to be reduced to form functionalities which are no longer amenable to transfer hydrogenation. These conditions are met by OH, SH, aryloxy, alkyloxy, arylthio, alkylthio, acyloxy, COOH, alkoxycarbonyl, acylamino, CN, NO$_2$, imine, olefinic double bonds and those conjugated with an electron donor (eg. enamines, enol ethers) or electron acceptor (Michael systems).

The process according to the invention for the enantioselective transfer hydrogenaton of prochiral ketones normally takes place by reacting the ketone with a hydrogen donor, preferably a secondary alcohol, in particular i-propanol, 2-butanol, cyclopentanol or cyclohexanol, specifically i-propanol, in the presence of catalytic amounts of one or more of the complexes according to the invention and catalytic amounts of a base. In this connection, the catalysts are employed in amounts of from 0.001 to 10 mol % per carbonyl group to be reduced, preferably 0.01 to 1 mol %, in particular 0.05 to 0.5 mol %. The amount of base, based on the catalyst, is in the range 0.5–100 mole equivalents, preferably 1–50 mol eq., in particular 5–30 mol eq. Suitable bases are alkali metal hydroxides, alkali metal $C_1$–$C_4$-alcoholates, alkali metal hydrides or calcium hydride. Alkali metal hydroxides or alcoholates are preferably employed. The reaction can be carried out in the secondary alcohol, if this is a liquid, as solvent. It is also possible, furthermore, especially when the solubility of the substrate demands this, to employ cosolvents, preferably ethers such as diethyl ether, tetrahydrofuran, methyl t-butyl ether, dioxane, pyran or hydrocarbons, light petroleum fractions, preferably hexane, and chlorinated hydrocarbons, for example dichlormethane or chloroform. The reaction is carried out in the range from −30° C. to 150° C., preferably 20° C. to 100° C., and, if the solvent has a lower boiling point, under pressure. The reaction time depends on the substrate and temperature and is in the range from 15 min to 12 h. The reaction mixture is worked up in a conventional way, and the product is isolated, for example, by distillation or crystallization.

In an alternative version of the process, a ruthenium complex according to the invention is generated from a suitable ruthenium precursor complex and a ligand $L^2$ of the general formula (III) in an inert solvent, eg. one of said cosolvents, and subsequently the prochiral ketone, the secondary alcohol and the base are added and the mixture is reacted.

The following examples are intended to illustrate the invention without restricting it.

EXAMPLES

General method for preparing the ruthenium complexes according to the invention of the general formula (I) with $X^1=X^2=Cl$, $L^1=P(C_6H_5)_3$ A solution of 0.3 mmol of a ligand $L^2$ of the general formula (IIId) (see Table 1) in 4 ml of anhydrous toluene was added to a solution of 0.3 mmol of tristriphenylphosphineruthenium(II) chloride [RuCl$_2$ (PPh$_3$)$_3$] in 6 ml of anhydrous toluene under an inert gas atmosphere, and the mixture was stirred at room temperature for about 12 h. The precipitate was filtered off with suction, washed with a little toluene and dried under reduced pressure. The catalysts indicated in the following Table 1 were obtained in this way as a brown powder in a yield of 55 to 90%.

Alternatively, after the reaction had taken place, the toluene was completely removed under reduced pressure, the residue was taken up in CHCl$_3$ and crystallization was induced by overlaying with hexane.

TABLE 1

(IIId)

Catalyst RuX$^1$X$^2$L$^1$L$^2$
$X^1=X^2=Cl$

| $L^1$ = PPh$_3$ | $R^4$ | $R^5$ | $R^6$ | Yield |
|---|---|---|---|---|
| Ex. 1 | Phenyl | Phenyl | i-Propyl | 72% |
| Ex. 2 | 2,2'-Biphenylene | | i-Propyl | 79% |
| Ex. 3 | Phenyl | Phenyl | t-Butyl | 75% |
| Ex. 4 | Phenyl | Phenyl | Methyl | |
| Ex. 5 | α-Naphthyl | α-Naphthyl | i-Propyl | |

The $^1$H- and $^{13}$C-NMR data for the complexes from Example 2 are as follows:

$^1$H NMR (300 MHz, CDCl$_3$): δ=0.69 [d,J=6.6Hz,3H,CH (CH$_3$)$_2$], 0.93 [d,J=6.7Hz,3H,CH(CH$_3$)$_2$], 2.05 [m,1H, CH(CH$_3$)$_2$], 4.54 (t,J=8.6Hz,1H,OCH$_A$H$_B$), 4.85 (dd,J= 8.6Hz,J=10.2Hz,1H,OCH$_A$H$_B$), 5.12 (dd,J=8.6Hz,J=8.3Hz, CHN=), 6.45 (dd,J=7.5Hz,J=8.2Hz,1H,Ar-H), 6.54 (d,J= 3.6Hz,1H,Ar-H), 7.01–7.08 (m,7H,Ar-H), 7.19–7.36 (m,13H,Ar-H), 7.51 (t,J=7.5Hz,1H,Ar-H), 7.62 (d,J=7.7Hz, 1H,Ar-H), 7.78 (d,J=8.0Hz,1H,Ar-H), 7.87 (t,J=8.2Hz,1H, Ar-H), 8,18 (dd,J=3.9Hz,J=3.5Hz,1H,Ar-H).

$^{13}$C NMR (75.5 MHz, CDCl$_3$): δ=17.84 [t,CH(CH$_3$)$_2$], 23.06 [t,CH(CH$_3$)$_2$], 32.34 [d,CH(CH$_3$)$_2$], 70.74 (t,OCH$_2$), 75,07 (CHN=), 120.18, 120.28, 120.99 (s,C-Ar), 121.08, 127.26, 127.38, 127.84, 127.98 (d,C-Ar), 128.76, 128.89 (s,C-Ar), 129.56, 130.18, 130.65, 130.85 (d,C-Ar), 130.96 (s,C-Ar), 131.57, 131.67 (d,C-Ar), 132.20, 133.18, 133.33 (s,C-Ar), 133.74, (d,C-Ar), 134.95, 134.30 (s,C-Ar), 134.58, 134.71 (d,C-Ar), 140.27, 141.65 (s,C-Ar).

General method for reducing prochiral ketones with the ruthenium complexes according to the invention.

0.01 mmol of catalyst (Tab. 2), 10 mmol of ketone (Tab. 2) and 0.25 mmol of solid KOH were successively added to 5 ml of 2-propanol, and the mixture was subsequently heated to reflux. The progress of the reaction was followed by gas chromatography. The acetone which had formed and excess 2-propanol were subsequently removed by distillation. To obtain the required product, the residue was subjected to vacuum distillation or crystallization. The results are compiled in Table 2.

TABLE 2

| Substrate | Catalyst | Reaction time | Product | Yield | (ee) |
|---|---|---|---|---|---|
| Aceto-phenone | Ex. 1 | 60 min | (R)-1-Phenyl-ethanol | 83% | 94% |
| Isobutyro-phenone | Ex. 2 | 30 min | (R)-1-Phenyl-2-methyl-propanol | 83% | 93% |
| Cyclohexyl methyl ketone | Ex. 3 | 60 min | (S)-1-Cyclo-hexylethanol | 70% | 60% |

Alternatively, the transfer hydrogenation can be carried out with a catalyst from one of Examples 1 to 5 which has been prepared in situ as follows.

0.01 mmol of tristriphenylphosphineruthenium(II) chloride [$RuCl_2(PPh_3)_3$] is introduced into 0.5 ml of anhydrous toluene, mixed with 0.013 mmol of the ligand $L^2$ (see Table 1) and stirred at room temperature for 0.5–20 h. Then 5 ml of isopropanol, 10 mmol of ketone and 0.25 mmol of base are added and the mixture is heated to reflux. The acetone which has formed and excess 2-propanol are subsequently removed by distillation. The required product is obtained by subjecting the residue to a vacuum distillation or crystallization.

We claim:

1. A chiral ruthenium complex of the formula (I),

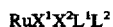

$$RuX^1X^2L^1L^2 \qquad (I)$$

where $X^1$ and $X^2$ are identical or different and are a halide ion, the anion of a $C_1$–$C_{10}$-carboxylic acid which may have 1, 2 or 3 chlorine or fluorine atoms, the anion of methanesulfinic acid or of trifluormethansulfinic acid, or $X^1$ and $X^2$ together are the dianion of a 1,3-, 1,4- or 1,5-dicarboxylic acid, $L^1$ is a cyclic ether with 5–6 ring atoms,
a cyclic olefin with 5–8 ring atoms,
an aromatic compound which may have 1, 2 or 3 alkyl groups as substituents,
CO, $PF_3$, isobutene or
a ligand of the general formula (II)

$$PR^1R^2R^3 \qquad (II)$$

where $R^1$, $R^2$ and $R^3$ are identical or different and are an alkyl group, cycloalkyl group or aryl group, which may have 1, 2 or 3 substituents which are selected, independently of one another, from $C_1$–$C_4$-alkyl groups or $C_1$–$C_4$-alkoxy groups, $L^2$ is a bidentate, chiral ligand of the general formula (III), (III)

where $R^4$ and $R^5$ are identical or different and are an alkyl group, cycloalkyl group or aryl group, which may have 1, 2 or 3 substitutents which are selected, independently of one another, from alkyl groups, alkoxy groups or halogen atoms, it also being possible for one of the $R^4$ or $R^5$ groups to be a hydrogen atom, or where $R^4$ and $R^5$ are, together with the phosphorus atom to which they are bonded, a saturated $C_5$–$C_7$-ring, which may be fused to one or two aryl rings, $R^6$ is an alkyl group which may have one or more groups which are selected from OH, SH, $NH_2$, COOH, aryloxy, alkoxy, arylthio, alkylthio, acyloxy, alkoxycarbonyl, acylamino, or an aralkyl group, hetaralkyl group, aryl group or hetaryl group, $R^7$ is hydrogen, an alkyl, aryl or aralkyl group, $R^8$ and $R^9$ are identical or different and are hyrogen, $C_1$–$C_4$-Alkyl or $C_1$–$C_4$-alkoxy groups, or $R^8$ and $R^9$ together are a fused cycloalkyl or aryl ring, where the absolute configuration at the carbon atoms which carry $R^6$ and $R^7$ is (S) or (R) independently of one another.

2. A complex as claimed in claim 1 of the formula (I) were $X^1$ and $X^2$ are identical or different and are halogen or the anion of a $C_1$–$C_4$-carboxylic acid.

3. A complex as claimed in claim 1 of the formula (I), where $L^1$ is a ligand of the formula (II).

4. A complex as claimed in claim 3, wherein in formula (II) $R^1$, $R^2$ and $R^3$ are identical or different and are $C_1$–$C_4$-alkyl, or phenyl, which is unsubstituted or substituted by $C_1$–$C_4$-alkyl.

5. A complex as claimed in claim 4, where $L^1$ is triphenylphosphine, tri-$C_1$–$C_4$-alkylphosphine, tritolylphosphine or trimesitylphosphine.

6. A complex as claimed in claim 1, where $R^4$ and $R^5$ in formula (III) are identical or different and are $C_1$–$C_4$-alkyl, in particular branched $C_1$–$C_4$-alkyl, aryl, which is unsubstituted or substituted by 1, 2 or 3 $C_1$–$C_4$-alkyl groups, or $R^4$ and $R^5$ together are n-butylene, n-pentylene or 2,2'-biphenylene.

7. A complex as claimed in claim 1, wherein $R^6$ in the formula (III) is $C_1$–$C_4$-alkyl, phenyl or $(CH_2)_nX$, where X is phenyl, 4-imidazolyl, 3-indolyl, α- or β-naphthyl, $NH_2$, OH, SH, $SCH_3$, COOH or COO-$C_1$–$C_4$-alkyl, and n is 1, 2 or 3.

8. A complex as claimed in claim 1 of the formula (I) where $X^1$ and $X^2$ are halogen and $L^1$ is triphenylphosphine.

9. A complex as claimed in claim 1, in which the chiral, bidentate ligand is a compound of the formulae (IIIa), (IIIb) or (IIIc),

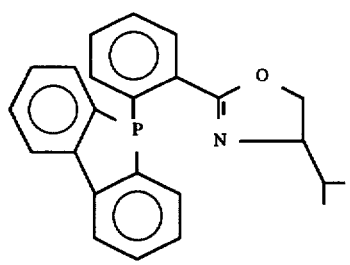
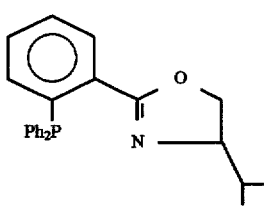
(IIIa)
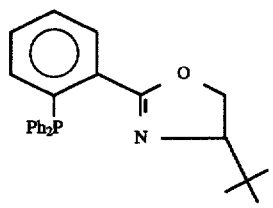
(IIIb)
(IIIc)
where the carbon atom which carries the alkyl group is uniformly (R) or (S).
* * * * *